(12) United States Patent
Gulliver et al.

(10) Patent No.: US 10,105,508 B2
(45) Date of Patent: Oct. 23, 2018

(54) HEADGEAR, INTERFACE AND AN ASSEMBLY

(75) Inventors: Laurence Gulliver, Auckland (NZ); Charles William Douglas Irving, Bristol (GB); Michael Paul Ronayne, Auckland (NZ)

(73) Assignee: Fisher & Paykel Healthcare Limited, Inc., Auckland (NZ)

( * ) Notice: Subject to any disclaimer, the term of this patent is extended or adjusted under 35 U.S.C. 154(b) by 1214 days.

(21) Appl. No.: 13/885,675

(22) PCT Filed: Nov. 16, 2011

(86) PCT No.: PCT/NZ2011/000242
§ 371 (c)(1),
(2), (4) Date: Jul. 29, 2013

(87) PCT Pub. No.: WO2012/067523
PCT Pub. Date: May 24, 2012

(65) Prior Publication Data
US 2013/0298912 A1    Nov. 14, 2013

Related U.S. Application Data

(60) Provisional application No. 61/414,346, filed on Nov. 16, 2010.

(51) Int. Cl.
*A61M 16/00* (2006.01)
*A61M 16/06* (2006.01)

(52) U.S. Cl.
CPC .... *A61M 16/0683* (2013.01); *A61M 16/0666* (2013.01); *A61M 2240/00* (2013.01)

(58) Field of Classification Search
CPC .......... A61M 16/0666; A61M 16/0683; A61M 2240/00
See application file for complete search history.

(56) References Cited

U.S. PATENT DOCUMENTS

| | | | |
|---|---|---|---|
| 6,470,886 B1 * | 10/2002 | Jestrabek-Hart | A61M 16/0683 128/207.11 |
| 6,889,689 B1 | 5/2005 | Neuman | |
| 7,296,575 B1 * | 11/2007 | Radney | A61M 16/06 128/207.11 |
| 2004/0083534 A1 | 5/2004 | Ruiz et al. | |
| 2007/0186931 A1 | 8/2007 | Zollinger et al. | |
| 2010/0218768 A1 | 9/2010 | Radney | |

FOREIGN PATENT DOCUMENTS

| | | |
|---|---|---|
| EP | 0 747 078 | 10/2002 |
| GB | 861574 | 2/1961 |
| WO | WO 2010/073142 | 7/2010 |

OTHER PUBLICATIONS

International Search Report; Application No. PCT/NZ2011/000242; dated Apr. 5, 2012; dated Apr. 12, 2012.

* cited by examiner

*Primary Examiner* — Bradley Philips
(74) *Attorney, Agent, or Firm* — Knobbe Martens Olson & Bear LLP

(57) ABSTRACT

This invention relates to a headgear comprising a semi-rigid frame engageable with the head of a user and a releasable connection system for releasable connection with a user interface, wherein the frame extends generally about a rear region of a user's head, generally about an upper region of a user's head, and generally about an ear or both ears of a user.

48 Claims, 6 Drawing Sheets

HEADGEAR, INTERFACE AND AN ASSEMBLY

INCORPORATION BY REFERENCE TO ANY PRIORITY APPLICATIONS

Any and all applications for which a foreign or domestic priority claim is identified in the Application Data Sheet as filed with the present application are hereby incorporated by reference herein in their entireties and made a part of the present disclosure.

FIELD OF THE INVENTION

The present invention generally relates to components for medical systems for conveying gases to and/or from a patient. In one particular aspect, the invention relates to headgear, a patient interface, or an assembly of headgear and a patient interface as part of a medical system for conveying breathable gases to and/or from a patient or as part of a breathing system.

BACKGROUND TO THE INVENTION

Alternative and improved retention systems for positioning, such as fixed positioning, of gas delivery interface systems, such as masks, nasal cannula or other oronasal gas delivery interface units, for a user of the interface are always being sought.

Typically, in infant applications, due to the size of the head of the infant, adhesive patches or other dermal connection systems are used to position such gas delivery interfaces. For example, adhesive tape is applied over the tube or part of a nasal cannula to hold the cannula in place or an operation position on the infant's face. This causes a number of problems, such as skin reactions, skin abrasion, or breakdown when tape is repeatedly applied and removed, especially when an infant is being cycled between different types of gas therapy.

Many complex systems, including elasticised straps, buckles, tensioners, and other such retaining systems, are utilised in holding or positioning of user interfaces on the face or in preferred installation positions on a user. Therefore, a system for improved ease of application or installation of such interfaces for a user, such as by the user or by a carer of the user are desirable. Ease of being able to cycle between different treatment therapies would also be desirable, especially also reducing the need for handling of a user's head or applying and re-applying adhesives, glues, or tapes to the face of the user for positioning of a gas delivery interface in an operational position.

Further, stresses applied to the head of a user from various complex headgears may result in stress sores or contact abrasion. Therefore, minimising the overall stresses applied to the head of a user is also desirable. Stresses applied to the head or face of a user, depending on where tension is exerted from such more complex headgear arrangements, can sometimes result in "snub nosing". The likelihood of snub nosing preferably is reduced or eliminated.

In this specification, any references to other patent specifications, other external documents, or other sources of information are generally for the purpose of providing a context for discussing the features of the invention. Unless specifically stated otherwise, reference to such external documents is not to be construed as an admission that such documents, or such sources of information, in any jurisdiction, are prior art, or form part of the common general knowledge in the art.

Further aspects and advantages of the present invention will become apparent from the ensuing description, which is given by way of example only.

SUMMARY OF THE INVENTION

It is therefore an object of the present invention to provide a headgear and/or an interface, or an assembly of both a headgear and an interface, which will go at least some way towards addressing the foregoing problems or which will at least provide the public with a useful choice.

In a first aspect, the present invention may broadly comprise a headgear comprising
a semi-rigid frame engageable with the head of a user, and
a releasable connection system for releasable connection with a user interface.

In a further aspect, the present invention may broadly comprise a headgear comprising
a semi-rigid frame engageable with the head of a user,
a releasable connection system for releasable connection with a user interface, wherein
the frame extends generally about a rear region of a user's head, generally about an upper region of a user's head, and generally about an ear or both ears of a user.

In one embodiment the releasable connection system may be provided on or about a region of the frame extending generally about the ear or ears of the user. In another embodiment the releasable connection system may be provided on or about a region of the frame extending generally in front of the ear or ears of the user. In another embodiment the releasable connection system may be provided as a region at or in front of the ear or ears of a user.

Preferably the releasable connection system may be a two-part connector system. More preferably, a first connector part or portion may be provided by, or on, a region of the headgear, and a second connector part or portion may be provided by, or on, a region of (or in attachment or connection with) a user interface.

In one embodiment the first connector part or portion is one of a hook or a loop of a hook and loop type fastener system, and the second connector part or portion is the other of a loop or a hook for the hook and loop type fastener system.

In another embodiment the two-part connector system is a system of magnets. Preferably the first connector part or portion is a first magnet or series of magnets, and the second connector part or portion is the other or a second magnet or series of magnets (e.g. such as a magnet or magnets of opposite polarity to the first magnet or series of magnets).

In another embodiment, the two-part connector system may be provided by a two-part adhesive, where the first connector part or portion is provided with an adhesive that is receivable by the second part or portion, or where the second connector part or portion is provided with an adhesive that is receivable by the first part or portion, or where the first part or portion provides for the first of a two-part adhesive, and the second part or portion provides for the second of a two-part adhesive, whereby the bringing together of the first and second parts or portions facilitates or enables adhesion between the two parts. Advantageously, the parts are releasably adherable to each other.

Preferably the first part comprises an adhesive and the second part is receivable of the adhesive or bondable with the adhesive, or the second part comprises an adhesive and the first part is receivable of the adhesive or bondable with the adhesive, or both the first and second parts comprise an adhesive or one part of a two-part adhesive. Optionally, such an adhesive is a releasable adhesive system, or is a non-permanent binding or bonding together of adhesive or adhesive receiver parts.

Preferably, the user interface may be a gas delivery system or a gas delivery device. More preferably the user interface may be a device for supplying of breathable gas to a user. Preferably the user interface may be any one or any combination of: mask, nasal cannula, oronasal device. Preferably the interface may be connectable to a breathing tube.

In one embodiment the releasable connection system may be of a substantially low or flat profile. In another embodiment the releasable connection system may be of a substantially similar profile to the profile of the frame. Preferably the profile is generally substantially planar or substantially flat (for example, may be planar or flat in profile).

Preferably the releasable connection system may be an interference attachment system. More preferably the interference attachment system provides for connection or connectability between a user interface (or a part thereof, or a part connected or attached to a user interface) and one or more of:

the headgear region extending generally about the ear or ears of a user, the headgear region extending generally in front of the ear or ears of a user, the headgear region at or in front of the ear or ears of a user.

Preferably the interference attachment system may be a two-part connector system as defined above.

In one preferred embodiment, advantageously, the releasable connection system does not utilise pulley strap systems or buckles. Pulley or buckle type systems can impact on a user's face, particularly an infant face. For example, application of a connection or retention system too tightly on a user's face may contribute to so-called "snub nosing", such as when forces are applied to the nose, septum or philtrum.

Preferably the releasable connection system enables connection between a user interface and the headgear, whilst reducing the likelihood of the application of tension during installation of the user interface to a user in combination with the headgear.

Preferably the releasable connection system reduces the likelihood of the need for application of adhesive, or adhesive tape, to a user's skin for the installation and placement of a user interface into an operational position, or may reduce the likelihood of the application of adhesive to a user's skin in installation or adhesive applied to a user's skin for connection of a user interface.

Preferably the frame extending generally about the ears of the user may partially or wholly surround or encircle one or both ears. More preferably the frame extending about the ear or ears of a user is a loop about an, or each, ear of the user.

Preferably the headgear may be adjustable.

Preferably the headgear may be provided in a ready-to-receive mode for receiving the head of a user and/or connecting with or connectable to/with a user interface (or a part or portion thereof).

Preferably the headgear may be provided in a ready-to-receive mode for receiving a user interface (or a part of a portion thereof).

Preferably the headgear may be adjustable for fitment to a user's head, such as for anatomical adjustment.

Preferably the headgear may be adjustable for different user head sizes.

Preferably the headgear may be adjustable for varying the distance the frame extends between the rear region (or region above the nape of a user's neck) and the portion of the frame that extends generally about the ear or ears of a user.

Preferably the headgear may be adjustable for varying the distance the frame extends between the upper region (or top) of a user's head and the portion of the frame that extends generally about the ear of ears of a user.

Preferably the frame extending generally about the ear or ears of a user may be adjustable, more preferably the loop about an, or each ear of the user, may be adjustable, such as adjustable by the size of the loop provided for encircling partially or wholly the ear or ears of a user.

Preferably the frame may include an adjustment strap or straps. Preferably the adjustment strap or one of the adjustment straps may be a part of the frame positionable generally about the upper region (or top) of the user's head. Alternatively the adjustment strap or one of the adjustment straps may be a part of the frame positionable generally about the rear region (or region above the nape of the user's neck). More preferably the adjustment straps may be both a part of the frame positionable generally about the upper region (or top) of the user's head and the frame positionable generally about the rear region (or above the nape region of the user's neck).

Preferably the adjustment strap or straps may be of a hook and loop type fastener system for adjustable fastening. More preferably, or alternatively, the adjustment strap or straps comprise or include a buckle arrangement, where an adjustment strap is insertable through a buckle.

Preferably the rear region may be a lower rear region of the user's head. More preferably the rear region may be a region above the nape of the user's neck.

Preferably the upper region may be a region about the top of a user's head.

Preferably the frame is formed of or from a semi-rigid material.

Preferably the frame is of a self-sustaining shape.

Preferably the frame is supportive of an interface which may be connected thereto.

Preferably the frame is provided as one-piece or as a single part article or is a unitary piece of headgear. For example, the frame preferably is not provided by multiple straps or multiple parts that must be assembled or connected together to provide the semi-rigid headgear.

Preferably the semi-rigid frame may be of a substantially non-elastic construction or substantially non-elastic material.

Preferably the frame may be of a substantially self-supporting shape and/or configuration.

Preferably the frame forms a semi-rigid frame about the head of a user.

Preferably the frame is supportive of an interface which may be connected thereto.

Preferably the frame provides a substantially self-supporting frame to which a user interface (or a part thereof, or a part connected or attached to a user interface) may be connectable and supported in-situ therefrom.

Preferably the releasable connection system may be capable of supporting shear and/or pull forces that may be imparted from connection of a user interface.

Preferably the frame may be of a substantially planar or substantially flat profile, the planar or flat profile generally contoured for planar or flat contact with a user's head.

Preferably the frame may be of a non-frayable woven material or fabric.

Preferably the frame may be of a non-woven material or fabric, alternatively may be of a semi-rigid polymer.

Preferably the frame may be formed of a thermoplastic or thermosetting polymeric material or composites therefrom. Alternatively, the frame may be formed of or from a weldable polymeric material.

Preferably the frame may be formed from a polyethylene terephthalate (PET), a polyethylene (PE), or polyester.

Preferably the frame may be formed from a non-woven polyethylene terephthalate (PET)/polyethylene (PE) laminated composite, or a non-woven PET/polyester laminated composite.

Preferably the headgear, or user interface, or both, are for an infant. More preferably, the headgear, or user interface, or both, are sized or designed for an infant.

In a further aspect, the present invention may broadly comprise a user interface comprising adapted for use with the headgear of the above aspects.

In a further aspect, the present invention may broadly comprise a user interface of the above aspect comprising:
 a user interfacing part or portion, and
 releasable connection system part or portion for releasable connection with a headgear connectable part or portion.

Preferably the releasable connection system part of portion may be provided by, or on, a region of (or in attachment or connection with) the user interface.

Preferably the releasable connection system part or portion may be integral with the user interfacing part or portion or may be over-moulded with the user interfacing part or portion.

Preferably the releasable connection system may form a backing or a substrate to which the user interface is attached or connected or connectable thereto.

Preferably, the user interface is provided with one or a pair (or more) of parts or portions connectable with the headgear. More preferably, a pair of parts or portions extend from a user interface for connection with the headgear.

Preferably the headgear connectable part or portion is substantially non-elastic.

Preferably the releasable connection system part or portion forms one part of a two-part connection system. More preferably the other of the two-part connection system may be provided by the frame (or headgear) ad defined above.

Preferably the releasable connection system may be a strip or a strap or a length of a connector part of the connection system. More preferably the strip or strap or length extends to be connectable to, or on, or about a region of the frame (or headgear) as defined above.

As discussed above, in one preferred embodiment, advantageously, the releasable connection system does not utilise pulley strap systems or buckles. Pulley or buckle type systems can impact on a user's face, particularly an infant face. For example, application of a connection or retention system too tightly on a user's face may contribute to so-called "snub nosing", such as when forces are applied to the nose, septum or philtrum.

Preferably the releasable connection system enables connection between a user interface and the headgear, whilst reducing the likelihood of the application of tension during installation of the user interface to a user in combination with the headgear.

Preferably, a first connector portion may be provided by, or on, a region of headgear (as defined above), and a second connector portion may be provided by, or on, a region of (or in attachment or connection with) the user interface.

In one embodiment the releasable connection system part or portion of the user interface may be of a substantially low profile. In another embodiment the releasable connection system part of portion of the user interface may be of a substantially similar profile to the profile of the frame. Preferably the profile is generally substantially planar or substantially flat (e.g. in profile).

Preferably the releasable connection system part or portion of the user interface may be an interference attachment system. More preferably the interference attachment system part or portion provides for connection or connectability between the user interface (or a part thereof, or a part connected or attached to a user interface) and one or more of:
 the headgear region extending generally about the ear or ears of a user,
 the headgear region extending generally in front of the ear or ears of a user,
 the headgear region at or in front of the ear or ears of a user.

Preferably the interference attachment system may be a two-part connector system as defined above.

Preferably, the user interface may be a gas delivery system or a gas delivery device. More preferably the user interface may be a device for supplying of breathable gas to a user.

Preferably the user interface may be any one or any combination of: mask, nasal cannula, oronasal device.

Preferably the user interface is held in a substantially fixed or operational position when in connection with the headgear.

Preferably the user interface is held in a substantially secure fixed or operational position when in connection with the headgear.

Preferably the interface may be connectable to a breathing tube.

Preferably the headgear, or user interface, or both, are for an infant. More preferably, the headgear, or user interface, or both, are sized or designed for an infant.

In a further aspect, the present invention may broadly compromise an assembly comprising:
 a headgear, the headgear as defined above, and
 a user interface, the user interface as defined above,
 the headgear and user interface releasably connectable to each other.

Preferably the headgear is supportive of the user interface in an in-situ or installed in-use position with or on a user of the interface.

Preferably the headgear may comprise a first part of a two-part releasable connection system, and the user interface or a region of (or in attachment or connection with) the user interface comprises a second of the two-part releasable connection system. More preferably, the first and second parts may be releasably connectable for retaining of the interface in a user in-use position, or configuration.

In one embodiment the first part is one of a hook or a loop of a hook and loop type fastener system, and the second part is the other of a loop or a hook for the hook and loop type fastener system.

In another embodiment the two-part connector system is a system of magnets. Preferably the first connector part or portion is a first magnet or series of magnets, and the second connector part or portion is the other or a second magnet or series of magnets (e.g. such as magnets of opposite polarity to the first magnet or series of magnets).

In another embodiment, the two-part connector system may be provided by a two-part adhesive, where the first connector part or portion is provided with an adhesive that is receivable by the second part or portion, or where the second connector part or portion is provided with an adhesive that is receivable by the first part or portion, or where the first part or portion provides for the first of a two-part adhesive, and the second part or portion provides for the second of a two-part adhesive, whereby the bringing together of the first and second parts or portions facilitates or enables adhesion between the two parts. Advantageously, the parts are releasably adherable to each other.

Preferably the first part comprises an adhesive and the second part is receivable of the adhesive or bondable with the adhesive, or the second part comprises an adhesive and the first part is receivable of the adhesive or bondable with the adhesive, or the both the first and second parts comprises an adhesive or one part of a two-part adhesive. Optionally, such an adhesive is a releasable adhesive system, or is a non-permanent binding or bonding together of adhesive or adhesive receiver parts.

Preferably the interface may be connectable to a breathing tube.

Preferably the headgear, or user interface, or both, are for an infant. More preferably, the headgear, or user interface, or both, are sized or designed for an infant.

The headgear and/or user interface of this invention may be utilised in combination or conjunction with any one or more of the inventions described in PCT/NZ2011/000218, the contents of which is herein incorporated by reference.

For the purposes of this specification, reference to "semi-rigid" may be defined as the headgear (or frame) having a form generally maintained by a structure or by materials selected to generally maintain a pre-determined shape or configuration, or which is generally self-supporting of its own weight and of a shape or form produced or formed during manufacture, construction or assembly of parts. Such a definition of semi-rigid includes the ability of such material to form to be able to be manipulated into alternative shapes or forms by adjustment of the relative parts or pieces making up the shape or form being semi-rigid themselves.

The term "comprising" as used in this specification means "consisting at least in part of". When interpreting each statement in this specification that includes the term "comprising", features other than that or those prefaced by the term may also be present. Related terms such as "comprise" and "comprises" are to be interpreted in the same manner.

This invention may also be said broadly to be embodied in the parts, elements and features referred to or indicated in the specification of the application, individually or collectively, and any or all combinations of any two or more said parts, elements or features, and where specific integers are mentioned herein which have known equivalents in the art to which this invention relates, such known equivalents are deemed to be incorporated herein as if individually set forth.

The invention is embodied in the foregoing and also envisages constructions of which the following gives examples only.

BRIEF DESCRIPTION OF THE DRAWINGS

Preferred embodiments of the invention will be described by way of example only and with reference to the drawings, in which.

DETAILED DESCRIPTION OF THE PREFERRED EMBODIMENTS

Figure 1:
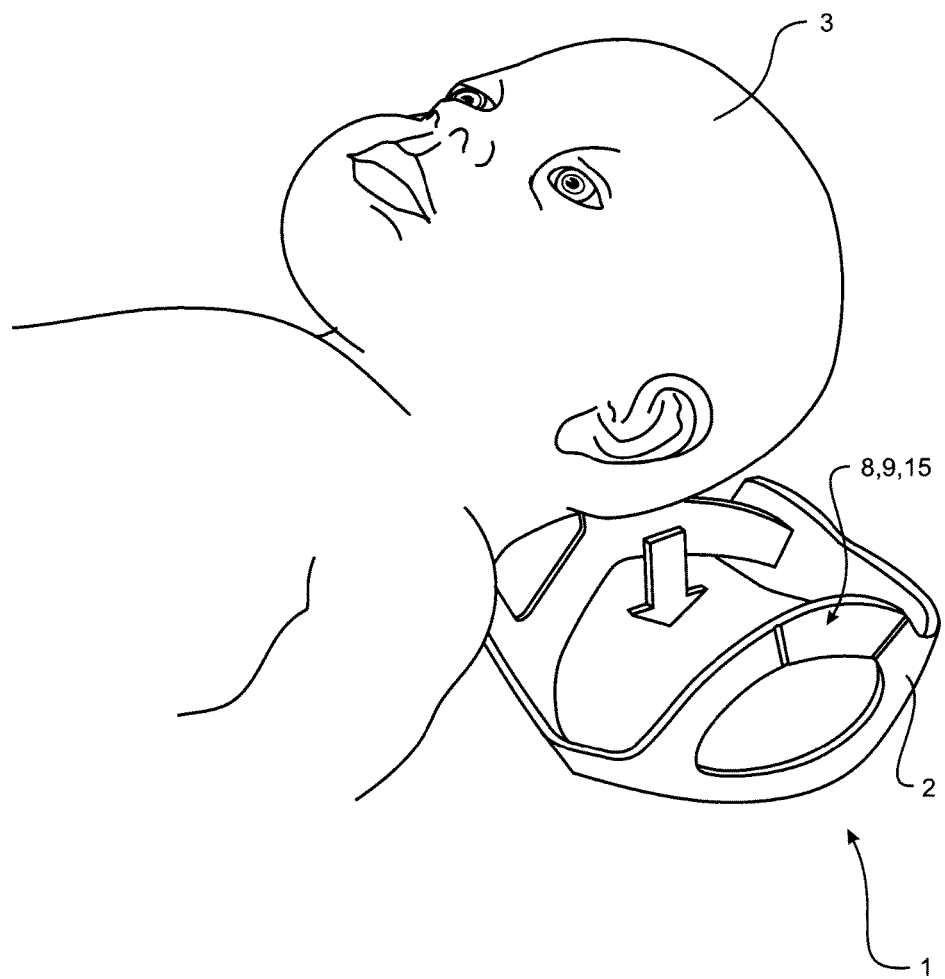
FIG. 1 shows a headgear according to one embodiment of the invention ready to receive the head of a user.

In one embodiment there is provided a headgear 1. Headgear 1 comprises a semi-rigid frame 2 engageable with the head 3 of a user, and a releasable connection system for releasable connection with a user interface 4.

The headgear 1 is easily and conveniently removable from, or installable on, the head 3 of a user. Advantageously, the semi-rigid nature of the headgear allows for resultant minimal handling of a user or user's head during installation of the headgear or installation of a user interface to a user to an operational position. Further, the present invention provides for improved security of maintaining the position a user interface with a user (e.g. prongs remaining in position in the nares of a user's nose) from the inter-connection of the user interface with the headgear.

It should be appreciated there are a number of disadvantages and problems associated with the need for re-positioning of an interface, particularly an infant interface. Included is "snub nosing", epidermal abrasion, or dermal allergies from traditional tapes or their adhesives. Such problems are also incurred during the cycling of a user between different treatment options and, traditionally, the subsequent need to remove headgear or tapes or user interfaces and then the installation of new equipment and user interfaces or interface positioning headgear or other gear.

Therefore, provision of a headgear that is in a ready-to-receive mode for receiving of a user's head or the user interface (or both) is a useful step in progressing toward reducing the problems users have previously been faced with. Further, improving the ease of installation, both in terms of complexity as well as time and effort by a carer (e.g. nurse), is of further benefit.

In a further embodiment headgear 1 comprises a semi-rigid frame 2 engageable with the head 3 of a user. The frame 2 extends generally about a rear region 5 of a user's head 3, generally about an upper region 6 of a user's head 3, and generally about an ear 7 or both ears 7 of a user. Such a frame 2 further comprises a releasable connection system for releasable connection with a user interface 4.

The releasable connection system can be on or about a region of the frame extending generally about the ear or ears of the user, or can be provided on or about a region of the frame extending generally at or in front of the ear or ears of the user, such as the region indicated by reference numeral 8.

The releasable connection system can be a two-part connector system. For example, a first connector part or portion 9 may be provided by, or on, a region of the headgear, such as for example region 8. A second connector part or portion 10 may be provided by, or on, a region of (or in attachment or connection with) a user interface, such as the region indicated by reference numeral 11.

FIG. 1 shows a headgear 1 in a configuration which is ready to receive the head 3 of a user.

Figure 6A:
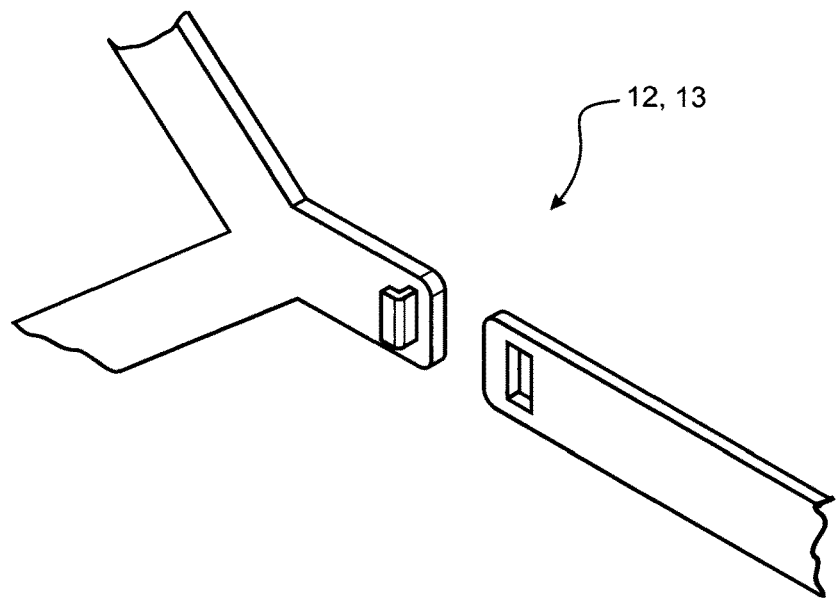
FIGS. 6*a* to 6*g* show different views of two-part connector systems which may be used to connect the headgear and interface.

It will be appreciated that various alternative releasable fastener or releasable type connection systems can be utilised with this invention. In one preferred embodiment, the first connector part or portion 9 can be a hook (or one of a hook or a loop) of a hook and loop type fastener system, and the second connector part or portion 10 would then be the loop (or other of a loop or a hook) for the complementary part of such a hook and loop type fastener system. In the embodiment shown in FIG. 6g, both first connector part 9 and second connector part 10 may include a mixture of hook and loop parts. Alternatively, a mushroom-type hook and loop fastener system may be used, as shown in FIG. 6d.

Figure 6B:
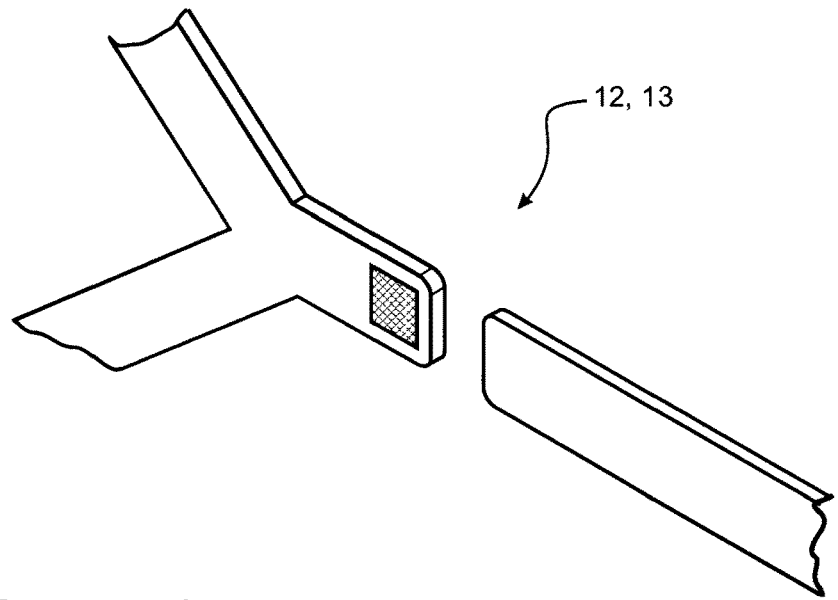

Alternatively, as for example shown in FIG. 6b, adhesive parts may be used where those adhesive parts are connectable to, or receivable of one another. For example, a first part 9 may be an adhesive part, or one part of a two-part adhesive connection system; and, the second part 10 may be a receiver of the first adhesive part, or the part 10 may be the second part of a two-part adhesive system. Such adhesives and parts 9, 10 are provided in a form so as to be releasable from each other.

Figure 6C:
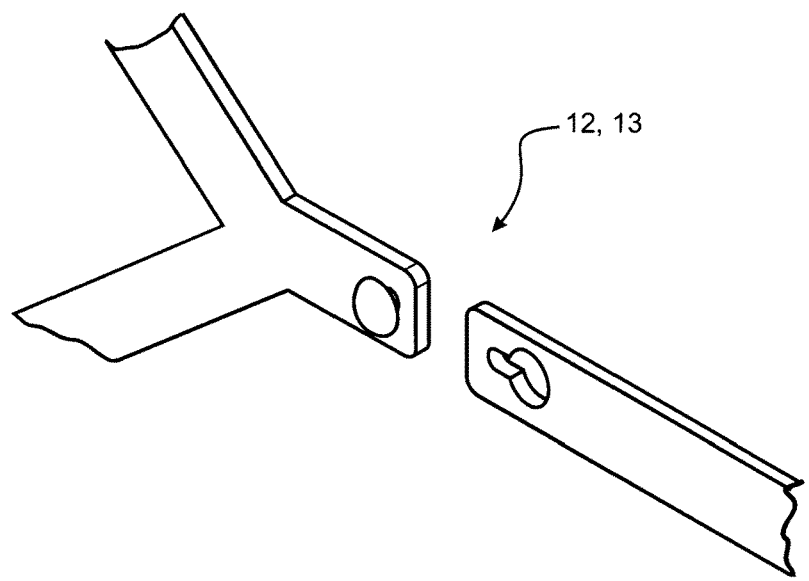
Figure 6D:
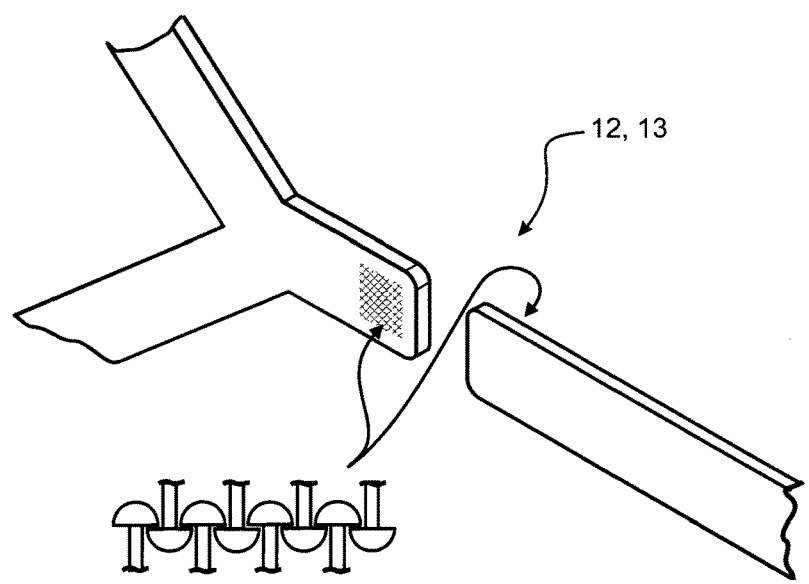
Figure 6E:
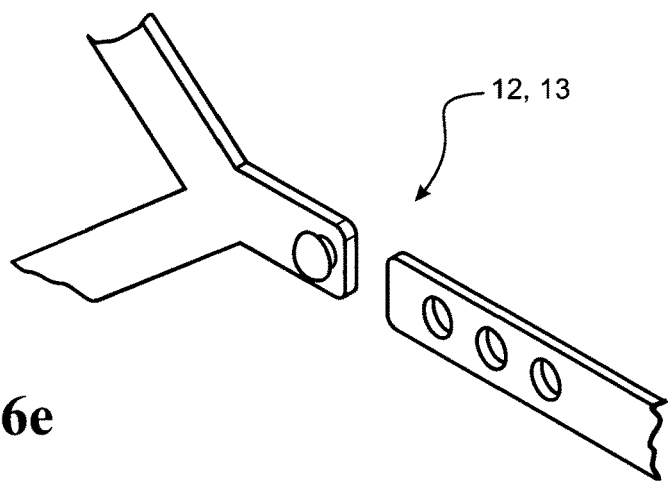
Figure 6F:
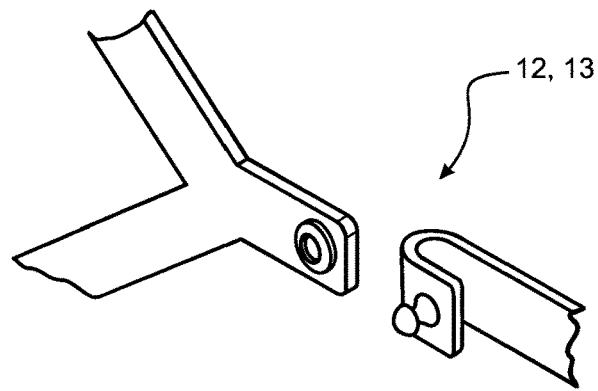
Figure 6G:
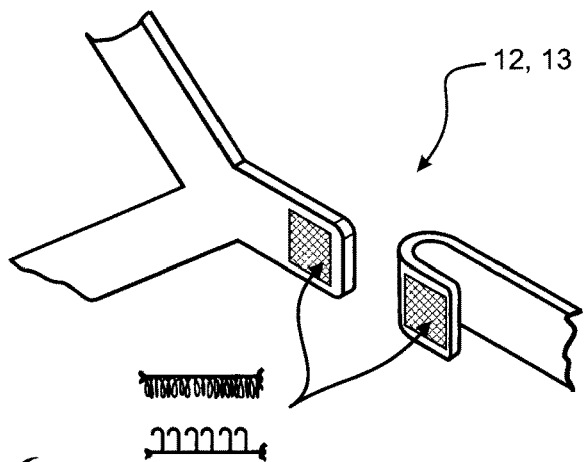

Further examples of releasable connection systems of other embodiments are shown in FIGS. 6a to 6g. As shown in FIG. 6a, first connector part 9 may include an L-shaped retaining hook, which can be inserted into a slot provided in second connector part 10. As shown in FIGS. 6c and 6e, first connector part 9 may include a dome which is shaped to fit into one or more slots in second connector part 10. The slots may be keyhole-shaped, to prevent accidental removal of the dome from the slot. Alternatively, as shown in FIG. 6f, a dome may be provided on second connector part 10, with a complementary receiver on first connector part 9.

FIGS. 6a-6g illustrate various embodiments of the releasable connection system, including variations of snap-fit or push-fit connection systems.

Advantageously, the releasable connection system utilised is of a substantially similar profile, or substantially similar to the profile of the frame 2. As shown in the figures, the profile is generally a substantially planar or substantially flat profile. This beneficially allows for increased comfort and minimising pressure sores, while minimising the visual impact or obstructions that other headgear of more raised exterior profiles may have or show. Part of the challenge in ensuring compliance with gas delivery systems by infant users is the visual impact that more obtrusive headgear or other systems have on the carers of the user or parents or guardians of infants.

For example, some prior art headgear systems are relatively obtrusive both in their overall size and visual impact. Such obtrusiveness and visual impact can be distressing to the carers or parents of infants undergoing treatment supplied by a user interface. It is therefore an aim of this invention to provide an alternative headgear system which aids in minimising obtrusiveness or visual impact to the carers of infants wearing such headgear, and/or which provides for a headgear and user interface set-up which is easier and less complex that those systems provided previously.

The releasable connection system can be of an interference attachment type system. For example, such an interference attachment system can provide for connection or connectability between a user interface 4 (or a part thereof, or a part connected or attached to a user interface) and the headgear 1, particularly to a region 8 that is either i) extending generally about the ear or ears 7 of the user, or ii) that is extending generally in front of the ear or ears of a user, or iii) at or in front of the ear or ears of a user.

Various types of releasable connection or attachment systems are contemplated. One example is that of a hook and loop type system, other systems may for example include other mechanical quick release systems.

In one preferred embodiment, advantageously, the releasable connection system does not utilise pulley strap systems or buckles. Pulley or buckle type systems can impact on a user's face, particularly an infant face, such as by pressure sores. For example, application of a connection or retention system too tightly on a user's face may contribute to so-called "snub nosing", such as when forces are applied to the nose, septum or philtrum. Such "snub nosing" is to be substantially avoided or reduced. This is uncomfortable for the user (particularly infant users), and distressing for the carer or parents of the infant. Therefore, the use of elasticised or stretchable materials is generally substantially avoided or reduced. For example, the headgear connectable part or portion of the user interface is of a substantially non-elastic part, thereby minimising or reducing the likelihood of any pre-loading of tension build-up between the user interfacing part and the user or user interfacing part and the headgear. At the same time, the user interface is generally maintained in an operational position (e.g. by maintaining the prongs of a nasal cannula in the nares of a user's nose). Then tension or forces between these parts can also be minimised or reduced.

Further, it is desirable for the releasable connection system to be enabled by a quick fit or quick release system or method for ease of installation or removal of the user interface from a user and to the headgear 1. Specifically, this invention reduces the likelihood of the need for application of tension during installation of the user interface to a user in combination with the headgear. Instead, the user interface can be placed into its required user interfacing position, the second connector or part of the user interface is then able to be quickly and relatively easily located upon the region of the headgear 1 adapted to receive the releasable connector region of the user interface. In this manner, a carer or installer of the user interface can, with ease and minimal need for additional help, install a user interface and locate the interface in its required operational position.

This invention beneficially reduces the likelihood of the need for application of adhesive, or adhesive tape, to a user's skin for the installation and placement of a user interface into an operational position. Adhesive tapes or other dermal adhesive patches, particularly for infants, create problems. Problems include, but are not limited to, skin irritation from adhesive chemicals (or adhesive removal chemicals, such as solvents) or tape materials (e.g. due to skin sensitivities), damage to user skin due to repeated application and removal of dermal patches or tapes for positioning or re-positioning of the interface for the user. Re-positioning may be required or adjustments may be needed where treatment therapies are being cycled (i.e. changed from one type of treatment to another, and then back again).

Advantageously therefore, this invention provides for a system of positioning or locating of a user interface for a user, yet reducing the likelihood of the problems associated with adhesive tapes attached to the user's skin.

In positioning of the user interface to the headgear 1, the frame 2 can extend generally about the ears of the user, may partially surround or encircle each, or both, ears, or may wholly surround or encircle the ear or both ears. The figures illustrate one embodiment where the ears are wholly encircled by loops. It will be appreciated that alternative shapes or forms are contemplated.

As more clearly shown by FIGS. 2-5, the headgear 1 can be adjustable. Adjustment allows for fitment to a user's head, such as for improved anatomical adjustment or differing head size.

The headgear 1 can be adjustable for varying the distance the frame 2 extends between the rear region 5 (or region above the nape of a user's neck) and the portion of the frame that extends generally about the ear or ears of a user.

The headgear 1 can alternatively, or in addition, be adjustable for varying the distance the frame extends between the upper region (or top) 6 of a user's head and the portion of the frame that extends generally about the ear of ears of a user.

In another alternative, or combination, the frame 2 extending generally about the ear or ears of a user can be adjustable, for example an adjustment can be made to the size of the loop about an, or each ear of the user. That is, the loop encircling partially or wholly the ear or ears of a user can be made smaller or larger, depending on the head 3 of a headgear user.

The various adjustments above can be made possible by an adjustment strap or straps.

Figure 2:
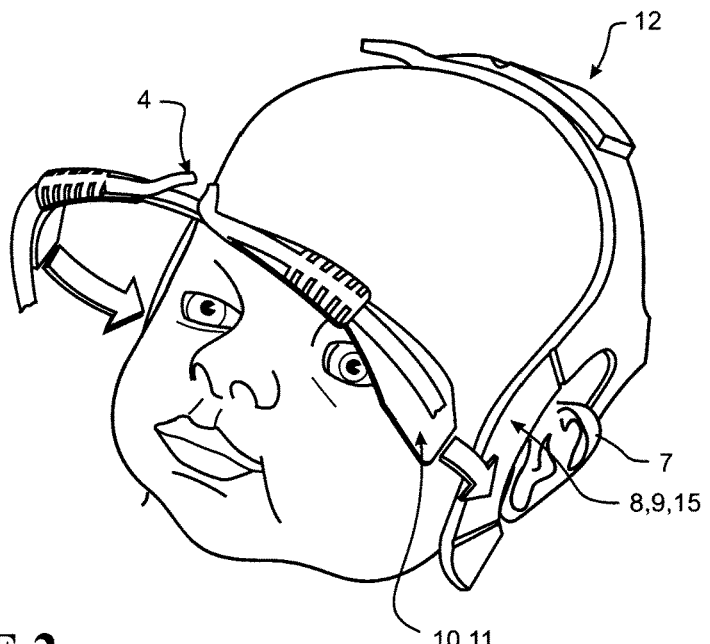
FIG. 2 shows a headgear in position about the head of a user, with a user interface ready to be positioned on a user and be connected to the headgear.
Figure 3:
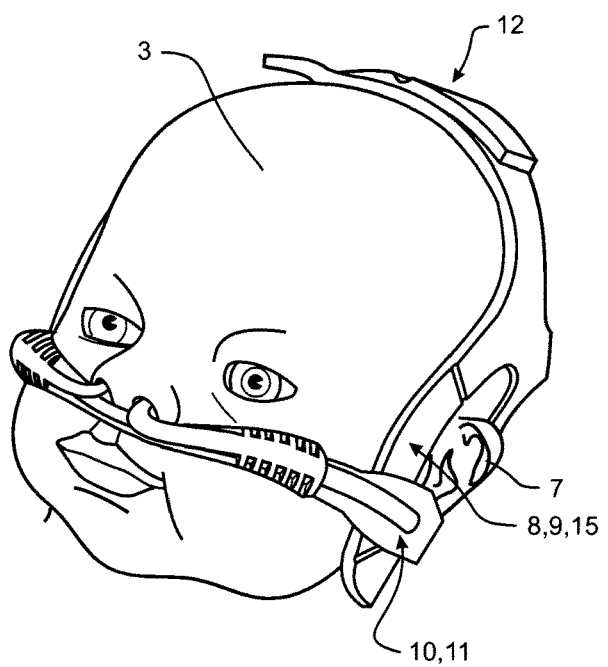
FIG. 3 shows an assembly of the headgear and user interface subsequent to interface positioning and connection of the interface with the headgear.
Figure 4:
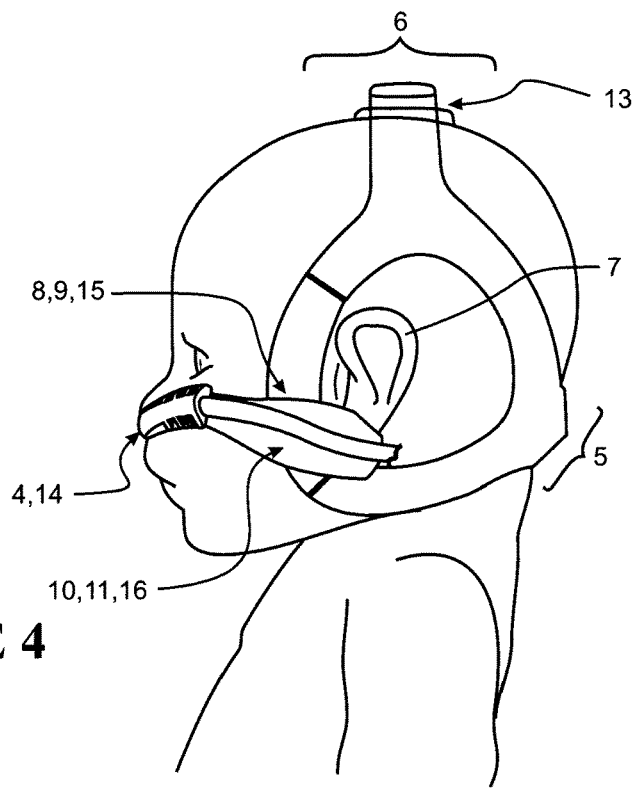
FIG. 4 shows a headgear with a user interface assembly in connection, demonstrated is connection of the interface to the headgear on a region of headgear in front of the ears of the user.
Figure 5:
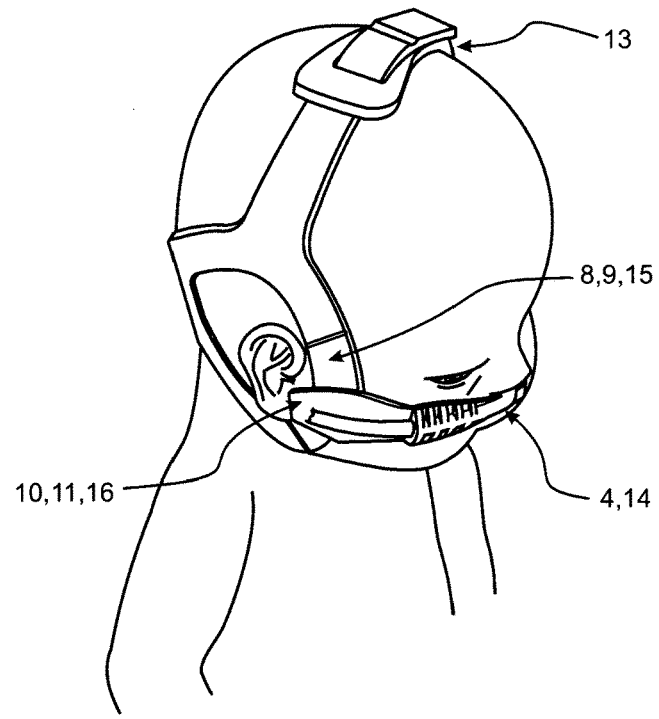
FIG. 5 shows a different view of the headgear and interface assembly of FIG. 4.

In one form, the adjustment strap or one of the adjustment straps may be that indicated by numeral 12 as being a part of the frame positionable generally about the upper region (or top) 6 of the user's head. Strap 12 is shown in FIGS. 2 and 3 as components that have reciprocal ones of a two-part releasable connection system, such as hook and loop components. Alternatively, FIGS. 4 and 5 illustrate an adjustment strap 13 in the form of a buckle arrangement where one of the adjustable straps is insertable through the buckle and positionable, again for example by use of a releasable connection system, such as that of a hook and loop type system being provided on an underside of the strap and connectable with an outward facing side of the buckle side of the strap.

Similar adjustment strap systems can be utilised for an adjustment strap or straps that are a part of the frame 2 and positionable generally about the rear region (or region above the nape of the user's neck) 5.

Such adjustment straps can be both a part of the frame 2 and positionable generally about the upper region (or top) 6 of the user's head and the frame positionable generally about the rear region (or region above the nape of the user's neck) 5. Optionally, included can be adjustment around the ear region.

With respect to the head 3 of the user, the rear region 5 is generally a lower rear region of the user's head, or generally the region above the nape of the user's neck. The upper region 6 is generally a region about the top of a user's head.

In another embodiment, the frame 2 can be a one-piece or a single part article or is a unitary piece of headgear. For example, the frame 2 is not provided by multiple parts that must be each assembled or connected together to provide the semi-rigid headgear.

In another embodiment, the frame 2 can be assembled into a headgear 1 which is semi-rigid, and being effectively a unitary piece of headgear, except for any optional adjustment straps. Optionally, the frame can be formed of all the same material.

Being of a semi-rigid form, it will be appreciated the frame 2 has an interface 4 which may be releasably connected thereto. Such self-supporting form of the headgear 1 allows for a distribution of any force applied to the headgear 1 from positioning of the interface. Such semi-rigid headgear 1 provides a frame 2 about which a user interface can be releasable connected thereto, and into which the head 3 of a user can be inserted.

In another exemplar, the semi-rigid frame can be formed of or from a substantially non-elastic construction or substantially non-elastic material. In this manner, the frame 2 is formed or constructed so as to be of a substantially self-supporting shape or configuration. In this manner, the frame provides a substantially self-supporting frame 2 to which a user interface 4 (or a part thereof, or a part connected or attached to a user interface) is connectable and supported in-situ therefrom.

The headgear 1 may be constructed to have the frame 2 being of a substantially planar or substantially flat profile. Such profile can allow for less bulky or obtrusive headgear, or can allow for wider distribution of any forces about a user's head. The flat or planar profile may contribute or allow for larger contouring of headgear 1 surface about the user's head 3. Similarly, the releasable connection system components are preferably of low profile for similar reasoning and reduced bulkiness.

The frame can be constructed or manufactured from various materials. Materials of a smooth surface or comfortable or soft outer material disposition for user may be preferred. Included are those materials of dermatological sensitivity.

In one embodiment, the headgear 1 can be constructed from non-woven materials, or those polymers providing suitable semi-rigidity. Other examples include forming of the frame from thermoplastic or thermosetting polymeric materials, or composites therefrom. Alternatively, the frame may be formed of or from a weldable polymeric material. Woven materials that do not fray easily, but which provide suitable semi-rigidity, may also be used.

Polyethylene terephthalate (PET), polyethylene (PE), or polyesters are other contemplated materials which may be formed into a suitably shaped frame 2. Similarly, the frame 2 may be formed from a non-woven polyethylene terephthalate (PET)/polyethylene (PE) laminated composite, or a non-woven PET/polyester laminated composite. Other laminate composites are also contemplated; suitable are those which provide for a level of semi-rigidity.

Particularly suited to this invention is the headgear, or user interface, or both, for infant use. Particularly this is due to their head size, need for delicate application of user interfaces or headgear with minimal disturbance to the infant, and desire to improve the ease of fitment of user interfaces to infants without the need for the more complicated systems currently available.

Such user interfaces are desirably those connectable to gas delivery systems for various breathing gas treatments, e.g. CPAP or other breathing gas treatments. User interfaces are any of those suitable as gas delivery devices, particularly those of masks, nasal cannula, or other oronasal devices.

In respect of a further embodiment there is provided a user interface 4. Such a user interface 4 comprises a user interfacing part or portion 14, and a headgear connectable part or portion 16.

In another embodiment however, there is provided the user interface 4 comprising the user interfacing part or portion 14, and a headgear connection system part or portion 16 for releasable connection with a releasable connectable part or portion 15. The headgear connection system may be provided by, or on, a region of (or in attachment or connection with) the user interface. In this manner, a part of the user interface or part that may be connected to the user interface part 16 may be supported by the releasable connection system part or portion 15 of the headgear. See for example FIGS. 2-5 in which the interface 14 is supported or attached to the portion 15. In some embodiments, interface 14 may be provided with one or a pair (or more) of parts or portions 16 connectable with the headgear, which parts or portions 16 may extend from interface 14 for connection with the headgear. In some embodiments, the releasable connectable part or portion 15 may be integral with the user interfacing part or portion 16 or may be over-moulded with the user interfacing part or portion 16.

The headgear connection system or its part or portion 16 can be in the form of a backing or a substrate to which the user interface is attached or connected or connectable thereto. Such a backing or substrate can extend across the whole back or skin-side of the user interface, or it may be attached or connected (or otherwise formed with) outer peripheral edges or sides of the user interface which then extend sufficient length to be enabled to releasably connect with the headgear 1 connectable part 15, for example on region 8.

Such part or portion 16 of the interface 4 is capable of supporting sufficient shear and pull forces exerted by positioning of the user interface and connecting of the part or portion 16 with the headgear 1 region 8. Sufficient connection strength or resistance is advantageously provided to limit or reduce the likelihood of an infant removing the part or portion 16 of the interface 4 from the headgear 1.

Desirably, suitable materials for such part or portion 16 are one or more of: dermatological appropriate/safe for skin contact (particularly for infant skin), smooth surfaced (to reduce or minimise abrasion to a user's skin), generally of a flat or planar profile (i.e. visually less obtrusive), and may be of a soft outer-most surface for improved feel to a user or carer or parent. Ideally, such materials may not produce lint, or be easily pilled, or easily frayable. Preferred materials also include those which allow for ease of cleaning.

The figures show the gas delivery tube connected to the user interface 4, 14. The gas delivery tube or any other tubes that may be connected to a user interface are optionally able to be freely positioned. Such tubes are not attached to the part 10 of the interface. The ability to independently position such tubes allows the carer (e.g. nurse) to arrange the tube or tubes in a manner most comfortable for the user to reduce the likelihood of pressure sores or other discomforts and reduce the likelihood of tubular kinking or other such situations.

As with the headgear 1, the headgear connection system part or portion 16 of the interface forms one (or a first) part of a two-part connection system. The other, or another, of the two-part connection system is then provided by the frame 2 (or headgear 1) as previously defined above. For example, one part can be one of a hook or a loop (of a hook and loop type releasable connection system), while the other part can the other of a loop or a hook, being the reciprocal connection part of such a hook and loop type system.

Such a headgear connection system part or portion of the user interface can be for example those which are an interference attachment system where a first part is interferingly attachable or connectable to a second part. Connection or connectability is desirably between the user interface (or a part thereof, or a part connected or attached to a user interface) and a headgear (as as that defined above), such as on or at one or more of: a headgear region extending generally about the ear or ears of a user; a headgear region extending generally in front of the ear or ears of a user; a headgear region at or in front of the ear or ears of a user.

Such headgear connection system part or portion 16 can be a strip or a strap or a length of a connector part of the connection system. Such strip or strap or length extends about or from around the user interface 14 to be connectable to or on or about a region of a frame, the frame (or headgear) as defined above. The releasable connection system part or portion 16 can be a flexible, yet non-elasticised part. In this manner, the portion 16 can be attached or connected to the frame 2 about for example region 8, 15, whilst not being overly stretchable, and therefore imparting tension forces to the user (particularly for reducing the likelihood of "snub nosing" problems).

In one preferred embodiment, advantageously, the releasable connection system does not utilise pulley strap systems or buckles. Pulley or buckle type systems can impact on a user's face, particularly an infant face. For example, application of a connection or retention system too tightly on a user's face may contribute to so-called "snub nosing", such as when forces are applied to the nose, septum or philtrum.

Beneficially the releasable connection system enables connection between a user interface and the headgear 1, whilst reducing the likelihood of the application of tension during installation of the user interface to a user in combination with the headgear.

A first connector portion 9 is provided by, or on, a region of headgear (as defined above), and a second connector portion 10 is provided by, or on, a region of (or in attachment or connection with) the user interface.

Again, with respect to the user interface, the user interface releasable connection system part or portion is advantageously of a substantially low profile, for example it may be a substantially similar profile to the profile of the frame (e.g. planar or flat).

The user interface may be any of those options mentioned previously above. In this invention, particularly preferred are user interface options for use with infants. Interfaces are connected to or connectable to gas delivery systems, especially breathable gas systems, and to other parts of a breathing system or medical circuit.

An assembly of the headgear 1 and user interface 4 provides for a system of improving comfort of a user and for aiming to improve compliance of treatment from user interfaces and gas delivery systems. In a further embodiment therefore, there is provided an assembly comprising a headgear 1, the headgear being as previously defined above. The assembly also comprises a user interface 4, the user interface being as previously defined above. The headgear 1 and user interface 4 are releasably connectable to each other.

As mentioned above, the headgear 1 is supportive or supporting of the user interface 4 in an interface 4 in-situ or installed in-use (or operational) position with or on a user. The headgear 1 is provided with a first or one part of a two-part releasable connection system, and the user interface 4, 14 or a region 16 of (or in attachment or connection with) the user interface comprises a second or other of the two-part releasable connection system. Such a system allows for the releasable retaining of the interface 4, 14 on a user.

The foregoing description of the invention includes preferred forms thereof. Modifications may be made thereto without departing from the scope of the invention.

What is claimed is:

1. A headgear for an infant, the headgear comprising:
   a semi-rigid frame engageable with the head of a user,
      wherein, in use, the semi-rigid frame extends about rear and upper regions of the user's head, and has an ear loop that partially or wholly surrounds or encircles one or both ears of the user, and wherein the semi-rigid frame is of a substantially self-supporting shape and/or configuration such that the semi-rigid frame maintains a pre-determined shape under its own weight; and a releasable connection system for releasable connection of the semi-rigid frame with a nasal cannula, the releasable connection system having a connected state and a disconnected state, the connected state being in which the nasal cannula is attached to the semi-rigid frame in-situ and ready for use, and the disconnected state being in which the nasal cannula is completely detached from the semi-rigid frame, the releasable connection system further comprising:

a first connecting region disposed on the semi-rigid frame, the first connecting region having a height and a lateral width, and a second connecting region disposed on the nasal cannula, the second connecting region having a longitudinal length, both the longitudinal length and the height being greater than the lateral width of the first connecting region, wherein, in the connected state, the second connecting region is positioned over the first connecting region and configured to directly engage the first connecting region by laying across the first connecting region such that a surface of the first connecting region facing away from the user is releasably fastened to a surface of the second connecting region facing toward the user, and wherein the first connecting region is configured to receive the second connecting region of the releasable connection system at any position within the second connecting region to reduce the likelihood of application of tension during installation of the nasal cannula to a user in combination with the semi-rigid frame, and wherein the releasable connection system is configured to have a non-elastic structure such that the nasal cannula is non-elastically attached to the semi-rigid frame through the releasable connection system.

2. The headgear as claimed in claim 1, wherein the releasable connection system is a two-part connector system.

3. The headgear as claimed in claim 1, wherein the first connecting region is one of a hook or a loop for a hook and loop type fastener system, and the second connecting region is the other of a loop or a hook for the hook and loop type fastener system.

4. The headgear as claimed in claim 1, wherein the releasable connection system is of a substantially low or flat profile.

5. The headgear as claimed in claim 1, wherein the releasable connection system is of a substantially similar profile to the profile of the frame.

6. The headgear as claimed in claim 1, wherein the semi-rigid frame is adjustable.

7. The headgear as claimed in claim 6, wherein the semi-rigid frame is adjustable for varying the distance the frame extends between the rear region and the portion of the frame that extends generally about the ear or ears of a user.

8. The headgear as claimed in claim 6, wherein the semi-rigid frame is adjustable for varying the distance the frame extends between the upper region of a user's head and the portion of the frame that extends generally about the ear or ears of a user.

9. The headgear as claimed in claim 6, wherein the frame extending generally about the ear or ears of a user is adjustable.

10. The headgear as claimed in claim 9, wherein the ear loop about an, or each, ear of the user is adjustable, such that the size of the loop provided for encircling partially or wholly the ear or ears of the user is adjustable.

11. The headgear as claimed in claim 1, wherein the semi-rigid frame includes an adjustment strap or straps.

12. The headgear as claimed in claim 11, wherein the adjustment strap or one of the adjustment straps is a part of the frame positionable generally about the upper region of the user's head.

13. The headgear as claimed in claim 11, wherein the adjustment strap or one of the adjustment straps is a part of the frame positionable generally about the rear region of the user's head.

14. The headgear as claimed in claim 11, wherein the adjustment strap or straps is of a hook and loop type fastener system for adjustable fastening.

15. The headgear as claimed in claim 12, wherein the upper region is a region about the top of a user's head.

16. The headgear as claimed in claim 1, wherein the semi-rigid frame is of a substantially non-elastic construction and/or substantially non-elastic material.

17. The headgear as claimed in claim 1, wherein the semi-rigid frame is of a substantially planar or substantially flat profile, the planar or flat profile generally contoured for planar or flat contact with a user's head.

18. The headgear as claimed in claim 1, wherein the semi-rigid frame is at least partially made of a woven material or fabric.

19. The headgear as claimed in claim 1, wherein the semi-rigid frame is at least partially made of a semi-rigid polymer.

20. The headgear as claimed in claim 1, wherein the semi-rigid frame is at least partially formed of a thermoplastic or thermosetting polymeric material or composites therefrom.

21. The headgear as claimed in claim 1, wherein the semi-rigid frame is at least partially formed of or from a weldable polymeric material.

22. The headgear as claimed in claim 1, wherein the semi-rigid frame is at least partially formed from a polyethylene terephthalate (PET), a polyethylene (PE), or polyester.

23. The headgear as claimed in claim 1, wherein the semi-rigid frame, or the nasal cannula, or both, are sized or designed for an infant.

24. The headgear as claimed in claim 1, wherein the second connecting region of the releasable connection system comprises a backing or a substrate to which the nasal cannula is attached or connected or connectable thereto.

25. The headgear as claimed in claim 1, wherein the second connecting region of the releasable connection system is substantially non-elastic.

26. The headgear as claimed in claim 1, wherein the second connecting region of the releasable connection system is of a substantially low profile.

27. The headgear as claimed in claim 1, wherein the nasal cannula is held in a substantially fixed or operational position when in connection with the semi-rigid frame.

28. The headgear as claimed in claim 1, wherein a portion of the longitudinal length of the second connecting region overhangs at least one side of the first connecting region, the longitudinal length of the second connecting region being greater than the lateral width of the first connecting region.

29. A headgear comprising:
a semi-rigid frame engageable with the head of a user, wherein the semi-rigid frame is of a substantially self-supporting shape and/or configuration such that the semi-rigid frame maintains a pre-determined shape under its own weight;

a releasable connection system having a first part for releasable connection with a second part provided on a respiratory interface and a third part for releasable connection with a fourth part provided on the respiratory interface;

wherein, in use, the semi-rigid frame extends generally about a rear region of a user's head, generally about an upper region of a user's head, and surrounds or encircles one or both ears of a user, wherein the first part of the releasable connection system spans a right region on the semi-rigid frame in front of a respective one of the user's ears, the right region having a lateral width, and the third part of the releasable connection system spans a left region on the semi-rigid frame in front of another respective one of the user's ears, the left region having a lateral width, and wherein the first part is configured to releasably engage the second part at any position within the right region and the third part is configured to releasably engage the fourth part at any position within the left region;

wherein the second part has a longitudinal length and the fourth part has a longitudinal length, the longitudinal length of the second part being greater than the lateral width of the right region, the longitudinal length of the fourth part being greater than the lateral width of the left region;

wherein the releasable connection system is configured to reduce application of tension applied to a face of the user during installation of the respiratory interface by laying the respiratory interface across the face of the user, laying the second part over the first part within the right region and engaging a mechanical connection therebetween, and laying the fourth part over the third part within the left region and engaging a second mechanical connection therebetween, such that the respiratory interface is non-elastically attached to the semi-rigid frame through the releasable connection system.

30. The headgear of claim 29, wherein the second part is configured to releasably engage the first part at any position within the region and at any angular orientation relative to the first part such that the position and orientation of the respiratory interface relative to the semi-rigid frame is variable.

31. The headgear of claim 29, wherein the first and second parts are configured to be releasably engaged by the quick-release connection in which movement along an axis engages and releases the second part from the first part.

32. The headgear of claim 31, wherein the first part is one of a hook or a loop for a hook and loop type fastener system, and the second part is the other of a loop or a hook for the hook and loop type fastener system.

33. The headgear of claim 31, wherein the first and second parts are configured to be releasably connected by snap-fitting or push-fitting.

34. The headgear of claim 29, wherein the first and second parts have a substantially planar or flat profile.

35. The headgear of claim 29, wherein the first and second parts have a substantially similar profile as the semi-rigid frame.

36. The headgear of claim 29, wherein attaching the second part to the first part at a position higher in the region on the semi-rigid frame in front of a respective one of the user's ears raises the respiratory interface relative to the semi-rigid frame, and attaching the second part lower in the region lowers the respiratory interface relative to the semi-rigid frame.

37. The headgear of claim 29, wherein attaching the first part to a portion of the second part that is closer to the respiratory interface positions the respiratory interface closer to the semi-rigid frame, and attaching the first part to a portion of the second part that is further from the respiratory interface positions the respiratory interface further from the semi-rigid frame.

38. The headgear of claim 29, wherein the first part is provided on a portion of the semi-rigid frame that faces away from the user.

39. A respiratory interface system for a user comprising:
a respiratory interface;
a headgear configured to engage the user's head, the headgear further comprising a semi-rigid frame having a self-supporting shape and/or configuration such that the semi-rigid frame maintains a pre-determined shape under its own weight, the semi-rigid frame extending around a rear region of a user's head, generally about an upper region of a user's head, and surrounds or encircles one or both ears of a user;
a first connector portion disposed on an outward facing surface of the headgear; and
a second connector portion having a longitudinal length and a connector height disposed on an inward facing surface of the interface,
wherein the first connector portion spans a region on the semi-rigid frame in front of a respective one of the user's ears, the region having a regional width and a regional height, the regional height being greater than the connector height, and
wherein the first connector portion is configured to releasably engage the second connector portion through a mechanical quick-release between the inward and outward facing surfaces by a single motion, the single motion being laying the second connector portion of the interface at a location along the regional height of the region of the first connector portion of the headgear, the single motion minimizing tension across a face of the user and requiring no further adjustment between the first and second connector portions.

40. The respiratory interface system of claim 39, wherein the second connector portion is configured to releasably engage the first connector portion at any position within the region and at any angular orientation relative to the first connector portion such that the position and orientation of the respiratory interface relative to the headgear is variable.

41. The respiratory interface system of claim 39, wherein the first and second connector portions are configured to be releasably engaged by the mechanical quick-release connection in which movement inward towards the user engages and movement outward from the user releases the second connector portion from the first connector portion.

42. The respiratory interface system of claim 41, wherein the first connector portion is one of a hook or a loop for a hook and loop type fastener system, and the second connector portion is the other of a loop or a hook for the hook and loop type fastener system.

43. The respiratory interface system of claim 41, wherein the first and second connector portions are configured to be releasably connected by snap-fitting or push-fitting.

44. The respiratory interface system of claim 39, wherein the second connector portion is configured to have a non-elastic structure such that the respiratory interface is non-elastically attached to the semi-rigid frame.

45. The respiratory interface system of claim 39, wherein the first and second connector portions have a substantially planar or flat profile.

46. The respiratory interface system of claim 39, wherein the first and second connector portions have a substantially similar profile as the semi-rigid frame.

47. The respiratory interface system of claim 39, wherein the first and second connector portions in combination with the semi-rigid frame are configured to reduce application of tension during installation of the respiratory interface to the user.

48. The respiratory interface system of claim 39, wherein attaching the second connector portion higher in the region of the at least one ear loop on the portion in front of the user's ear raises the respiratory interface relative to the headgear, and attaching the second connector portion lower in the region lowers the respiratory interface relative to the headgear.

\* \* \* \* \*